United States Patent
Grady et al.

(10) Patent No.: US 10,314,655 B2
(45) Date of Patent: Jun. 11, 2019

(54) SYSTEMS AND METHODS FOR PROVIDING PERSONALIZED ESTIMATES OF BIOHEAT TRANSFER

(71) Applicant: HeartFlow, Inc., Redwood City, CA (US)

(72) Inventors: Leo Grady, Millbrae, CA (US); Charles A. Taylor, Menlo Park, CA (US); Christopher K. Zarins, Menlo Park, CA (US)

(73) Assignee: HeartFlow, Inc., Redwood City, CA (US)

( * ) Notice: Subject to any disclaimer, the term of this patent is extended or adjusted under 35 U.S.C. 154(b) by 0 days.

(21) Appl. No.: 15/088,626

(22) Filed: Apr. 1, 2016

(65) Prior Publication Data
US 2016/0287338 A1 Oct. 6, 2016

Related U.S. Application Data (60) Provisional application No. 62/141,911, filed on Apr. 2, 2015.

(51) Int. Cl.
| | | |
|---|---|---|
| *G06F 19/00* | (2018.01) | |
| *A61B 34/00* | (2016.01) | |
| *A61B 34/10* | (2016.01) | |
| *A61B 18/00* | (2006.01) | |
| *A61B 18/12* | (2006.01) | |
| *G16H 50/50* | (2018.01) | |
| *A61F 7/00* | (2006.01) | |
| *A61N 7/02* | (2006.01) | |
| *A61B 18/02* | (2006.01) | |

(52) U.S. Cl.
CPC .............. *A61B 34/10* (2016.02); *A61B 34/00* (2016.02); *G06F 19/00* (2013.01); *G16H 50/50* (2018.01); *A61B 18/02* (2013.01); *A61B 18/12* (2013.01); *A61B 2018/00577* (2013.01); *A61B 2034/104* (2016.02); *A61F 7/00* (2013.01); *A61N 7/02* (2013.01)

(58) Field of Classification Search
None
See application file for complete search history.

(56) References Cited

U.S. PATENT DOCUMENTS

| | | | |
|---|---|---|---|
| 8,315,812 B2 | 11/2012 | Taylor | |
| 8,918,162 B2 | 12/2014 | Prokoski | |
| 9,259,287 B2* | 2/2016 | Mansi | ............... A61B 34/10 |
| 2014/0136174 A1 | 5/2014 | Audigier et al. | |
| 2014/0296842 A1* | 10/2014 | Mansi | ............... A61B 19/50 606/34 |
| 2015/0294082 A1 | 10/2015 | Passerini et al. | |

OTHER PUBLICATIONS

Arkin et al. (IEEE Transactions on Biomedical Engineering (1994) vol. 41:97-107).*
Bhowmik et al. (Journal of Thermal Biology (2013) vol. 38:107-125).*
Kok et a. (International Journal of Hyperthermia (2013) vol. 29:336-345.*
Majchrzak et al. (Scientific Research of the Institute of Mathematics and Computer Science (2010) vol. 9:145-152.*
Majchrzak et al. (Computer Assisted Methods in Engineering and Science (2013) vol. 20:123-131.*
Rossman et al. (Visualization, Image Processing, and Computation in Biomedicine (2012) vol. 1:e—pp. 1-9).*
Vignon-Clementel et al. (Computer Methods in Biomechanics and Biomedical Engineering (2010) iFirst article, pp. 1-16).*
H. Petra Kok et al.: "Thermal modelling using discrete vasculature for thermal therapy: A review", International Journal of Hyperthermia, vol. 29, No. 4, Jun. 1, 2013 (Jun. 1, 2013), pp. 336-345.
International Search Report and Written Opinion for corresponding Application No. PCT/US2016/025567 dated Jul. 4, 2016 (14 pages).

* cited by examiner

*Primary Examiner* — Lori A. Clow
(74) *Attorney, Agent, or Firm* — Bookoff McAndrews, PLLC (57) ABSTRACT

Systems and methods are disclosed for providing personalized estimates of bioheat transfer through a patient's body or a portion of a patient's body. One method includes receiving a patient-specific vascular model of a patient's anatomy, including at least one vessel of the patient; receiving a patient-specific tissue model including at least a portion of tissue of the patient's anatomy; receiving an estimate of heat content of the portion of tissue of the patient-specific tissue model or tissue surrounding the portion of tissue; determining an estimate of heat distribution of the portion of tissue of the patient-specific tissue model or tissue surrounding the portion of tissue based on the vascular model, the tissue model, or the received estimate of heat content; and output the determined estimate of heat distribution to a storage medium or user display.

20 Claims, 7 Drawing Sheets

SYSTEMS AND METHODS FOR PROVIDING PERSONALIZED ESTIMATES OF BIOHEAT TRANSFER

RELATED APPLICATION(S)

This application claims priority to U.S. Provisional Application No. 62/141,911 filed Apr. 2, 2015, the entire disclosure of which is hereby incorporated herein by reference in its entirety.

FIELD OF THE DISCLOSURE

Various embodiments of the present disclosure relate generally to disease assessment, treatment planning, and related methods. More specifically, particular embodiments of the present disclosure relate to systems and methods of providing personalized estimates of bioheat transfer through a patient's body or a portion of a patient's body.

BACKGROUND

The human body has a refined homeostatic mechanism for maintaining constant body temperature, but it nevertheless may be sensitive to external temperature. Some temperature changes may affect the whole body and cause conditions that may be potentially life-threatening, for example, hypothermia, hyperthermia, heat stroke, and/or heat exhaustion. These conditions may be treated through a variety of methods, for example, rewarming, fluid ingestion, immersion in warm/cool water, or by more advanced mechanisms. Other temperature changes may be applied focally as therapeutics, for example, applying radiofrequency (RF) ablation or cryoablation to treat cancer or to treat atrial fibrillation or ventricular tachycardia. In these cases, extreme temperatures may be used to deliberately damage pathological tissue while trying to preserve surrounding healthy tissue. However, heat transfer in the human body may be complex and difficult to predict since heat transfer may be contingent on a variety of factors including, for example, heat diffusion through multiple different materials (e.g., tissue, fluid, bone), the convection of the vascular system, and/or temperatures external to the body. In addition, individuals' bodies may vary in their abilities to adjust or regulate temperatures, which may cause people to vary in how prone they are to heat-related illness or how sensitive they are to treatment.

Thus, a desire exists for understanding bioheat transfer specific to an individual. For example, a desire exists to model bioheat (e.g., heat transfer or heat distribution) in an individual's entire body and/or in isolated organs and body parts. Furthermore, a desire exists to evaluate effectiveness of temperature-related treatments.

The foregoing general description and the following detailed description are exemplary and explanatory only and are not restrictive of the disclosure.

SUMMARY

According to certain aspects of the present disclosure, systems and methods are disclosed providing personalized estimates of bioheat transfer through a patient's body or a portion of a patient's body.

One method includes: receiving a patient-specific vascular model of a patient's anatomy, including at least one vessel of the patient; receiving a patient-specific tissue model including at least a portion of tissue of the patient's anatomy; receiving an estimate of heat content of the portion of tissue of the patient-specific tissue model or tissue surrounding the portion of tissue; determining an estimate of heat distribution of the portion of tissue of the patient-specific tissue model or tissue surrounding the portion of tissue based on the vascular model, the tissue model, or the received estimate of heat content; and output the determined estimate of heat distribution to a storage medium or user display.

In accordance with another embodiment, a system for providing personalized estimates of bioheat transfer through a patient's body or a portion of a patient's body comprises: a data storage device storing instructions for providing personalized estimates of bioheat transfer through a patient's body or a portion of a patient's body; and a processor configured for: receiving a patient-specific vascular model of a patient's anatomy, including at least one vessel of the patient; receiving a patient-specific tissue model including at least a portion of tissue of the patient's anatomy; receiving an estimate of heat content of the portion of tissue of the patient-specific tissue model or tissue surrounding the portion of tissue; determining an estimate of heat distribution of the portion of tissue of the patient-specific tissue model or tissue surrounding the portion of tissue based on the vascular model, the tissue model, or the received estimate of heat content; and output the determined estimate of heat distribution to a storage medium or user display.

In accordance with another embodiment, a non-transitory computer readable medium for use on a computer system containing computer-executable programming instructions for performing a method of providing personalized estimates of bioheat transfer through a patient's body or a portion of a patient's body, the method comprising: receiving a patient-specific vascular model of a patient's anatomy, including at least one vessel of the patient; receiving a patient-specific tissue model including at least a portion of tissue of the patient's anatomy; receiving an estimate of heat content of the portion of tissue of the patient-specific tissue model or tissue surrounding the portion of tissue; determining an estimate of heat distribution of the portion of tissue of the patient-specific tissue model or tissue surrounding the portion of tissue based on the vascular model, the tissue model, or the received estimate of heat content; and output the determined estimate of heat distribution to a storage medium or user display.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments, and together with the description, serve to explain the principles of the disclosed embodiments.

DESCRIPTION OF THE EMBODIMENTS

Reference will now be made in detail to the exemplary embodiments of the disclosure, examples of which are illustrated in the accompanying drawings. Wherever possible, the same reference numbers will be used throughout the drawings to refer to the same or like parts.

As described above, a desire exists for understanding bioheat transfer specific to an individual. For example, the capability to model bioheat (e.g., heat transfer or heat distribution) in a patient's body may improve an evaluation of the severity of disease and of the appropriateness of treatment.

This disclosure describes systems and methods for determining bioheat transfer in a patient by modeling the effects of blood flow, tissue, and the external environment on the distribution of heat in the patient's body. For example, the systems and methods may address both bioheat modeling throughout the patient's body and/or the modeling of bioheat transfer in isolated organs and body parts. It should be appreciated that any of the following techniques and descriptions should be construed to include analysis of heat transfer through a patient's entire body, an entire organ of the patient's body, or one or more parts of the body or organs. The embodiments of this disclosure may permit planning and assessing the effectiveness of temperature-related treatments for a patient, e.g., in the relief of whole body temperature conditions or focally-applied therapeutics. By extension, the embodiments of this disclosure provide assessments or recommendations of effective temperature-related treatment and aid the design and development of new temperature-related treatments and devices.

Figure 1:
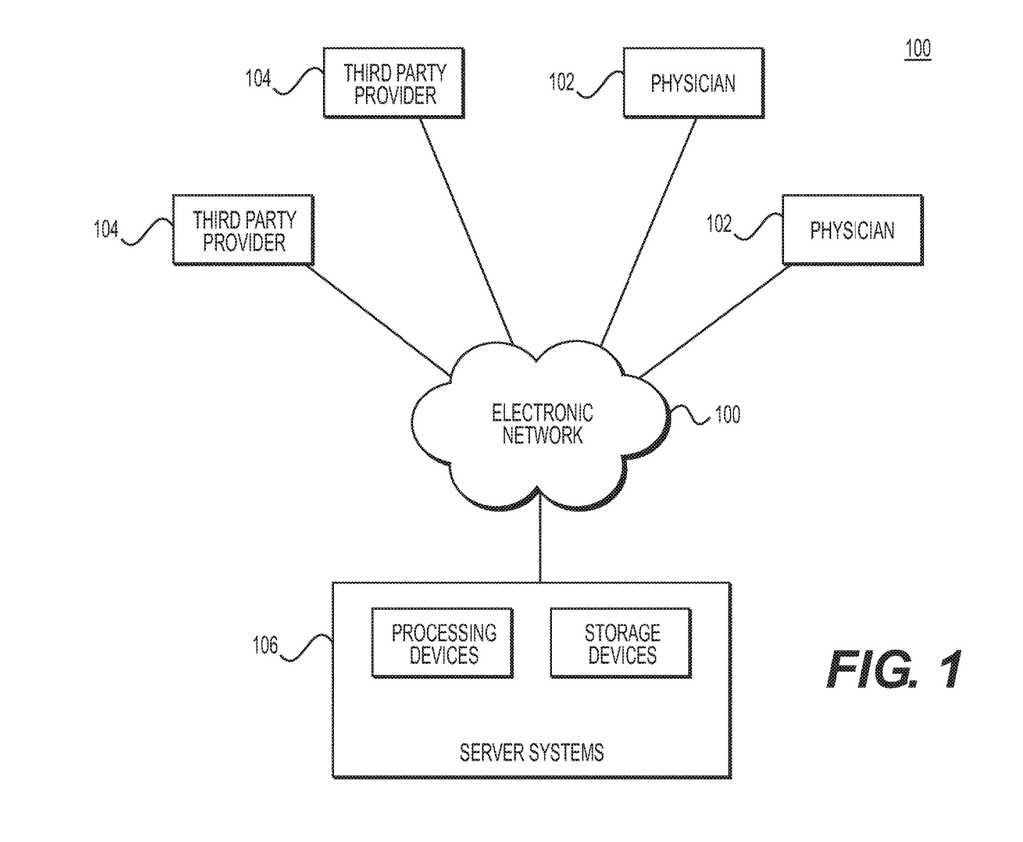
FIG. 1 is a block diagram of an exemplary system and network for providing personalized estimates of bioheat transfer through a patient's body or a portion of a patient's body, according to an exemplary embodiment of the present disclosure.

Referring now to the figures, FIG. 1 depicts a block diagram of an exemplary system 100 and network for providing personalized estimates of bioheat transfer through a patient's body or a portion of a patient's body, according to an exemplary embodiment. Specifically, FIG. 1 depicts a plurality of physicians 102 and third party providers 104, any of whom may be connected to an electronic network 101, such as the Internet, through one or more computers, servers, and/or handheld mobile devices. Physicians 102 and/or third party providers 104 may create or otherwise obtain images of one or more patients' anatomy. The physicians 102 and/or third party providers 104 may also obtain any combination of patient-specific information, e.g., age, medical history, blood pressure, blood viscosity, body temperature, patient activity or exercise level, etc. Physicians 102 and/or third party providers 104 may transmit the anatomical images and/or patient-specific information to server systems 106 over the electronic network 101. Server systems 106 may include storage devices for storing images and data received from physicians 102 and/or third party providers 104. Server systems 106 may also include processing devices for processing images and data stored in the storage devices. For the purposes of the disclosure, "patient" may refer to any individual or person for whom diagnosis or treatment analysis is being performed, or any individual or person associated with the diagnosis or treatment analysis of one or more individuals.

Figure 2:
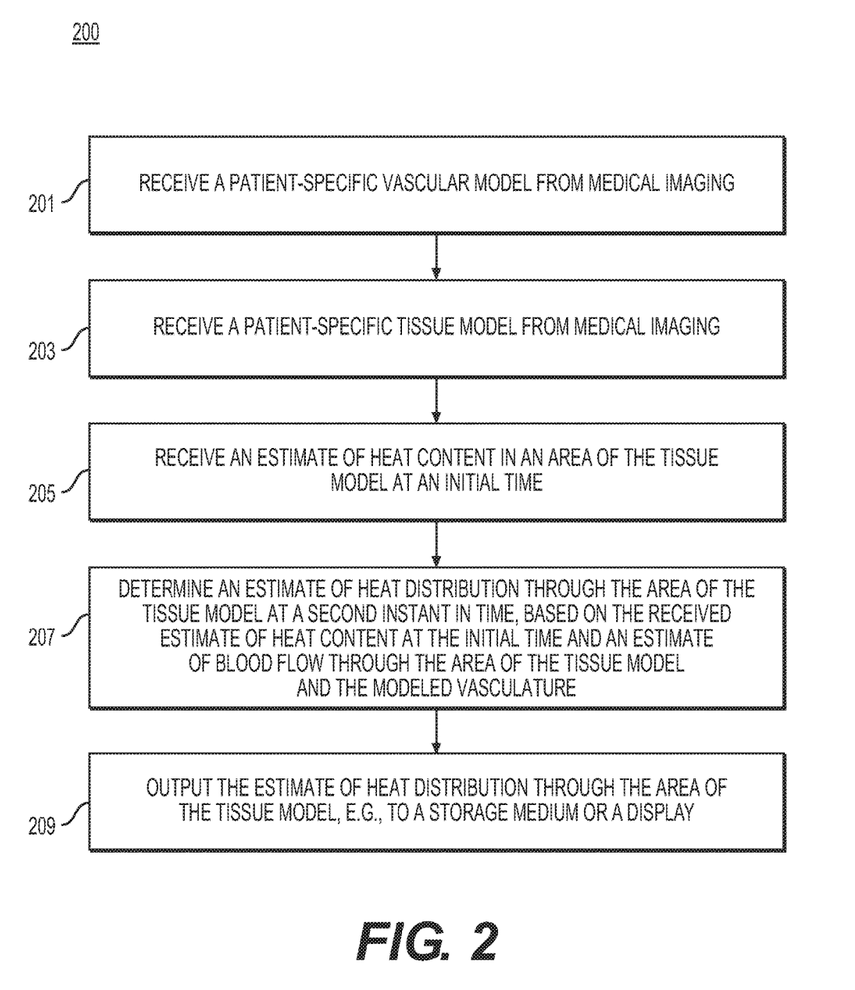
FIG. 2 is a flow diagram of an exemplary method of providing personalized estimates of bioheat transfer through a patient's body or a portion of a patient's body, according to an exemplary embodiment of the present disclosure.
Figure 3:
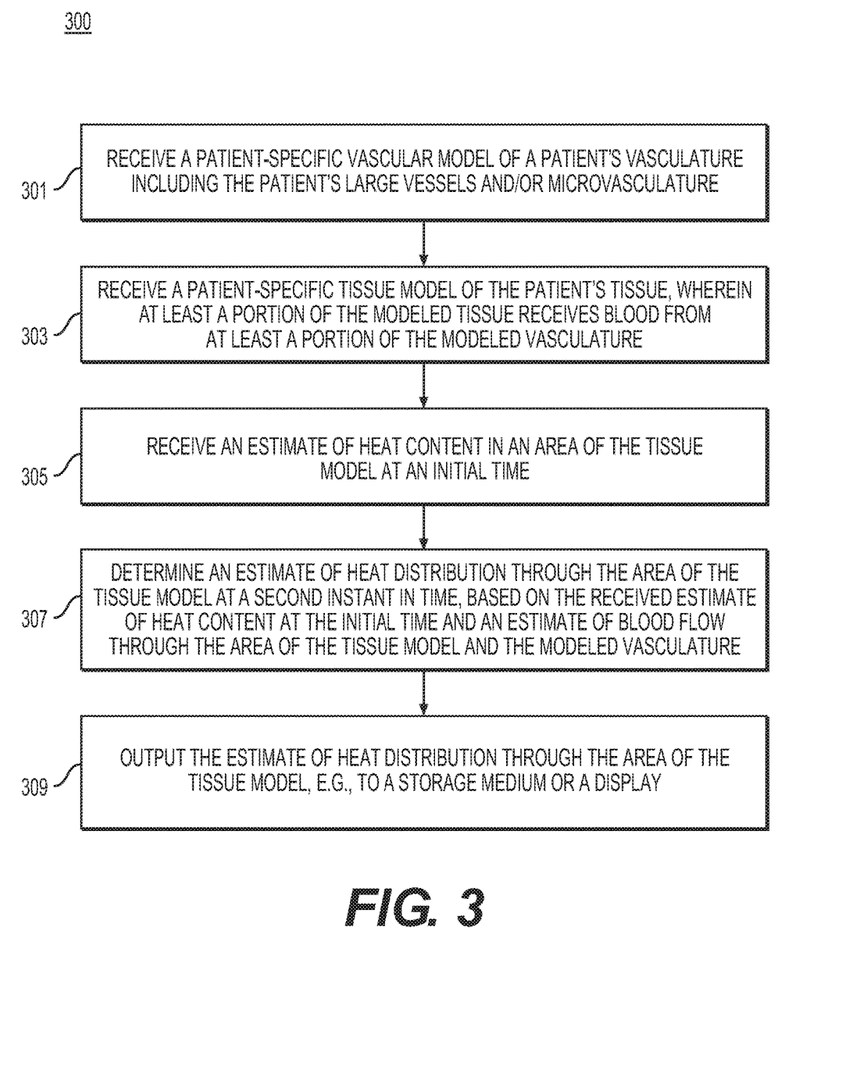
FIG. 3 is a flow diagram of an exemplary method of generating personalized examples of heat transfer in a patient's body, according to an exemplary embodiment of the present disclosure.
Figure 4:
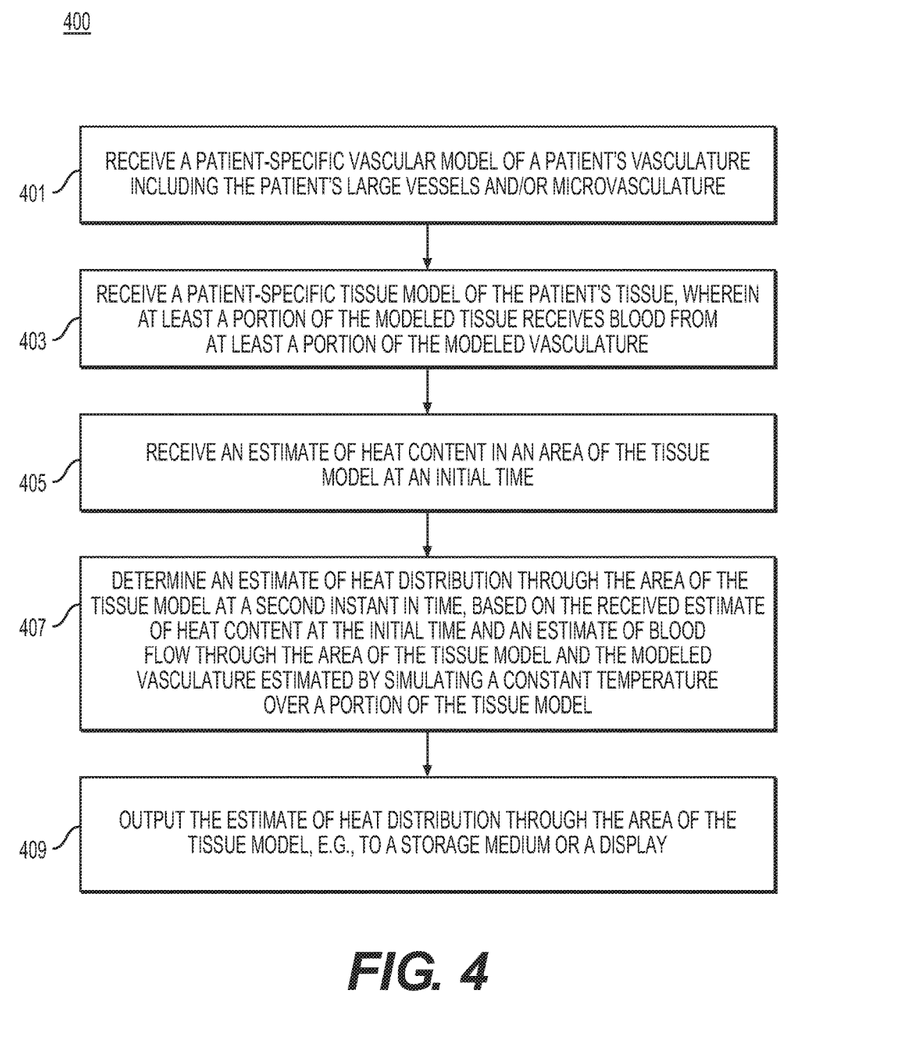
FIG. 4 is a flow diagram of an exemplary method of generating personalized examples of heat transfer in a patient's body involving rapid changes in body temperature, according to an exemplary embodiment of the present disclosure.
Figure 5A:
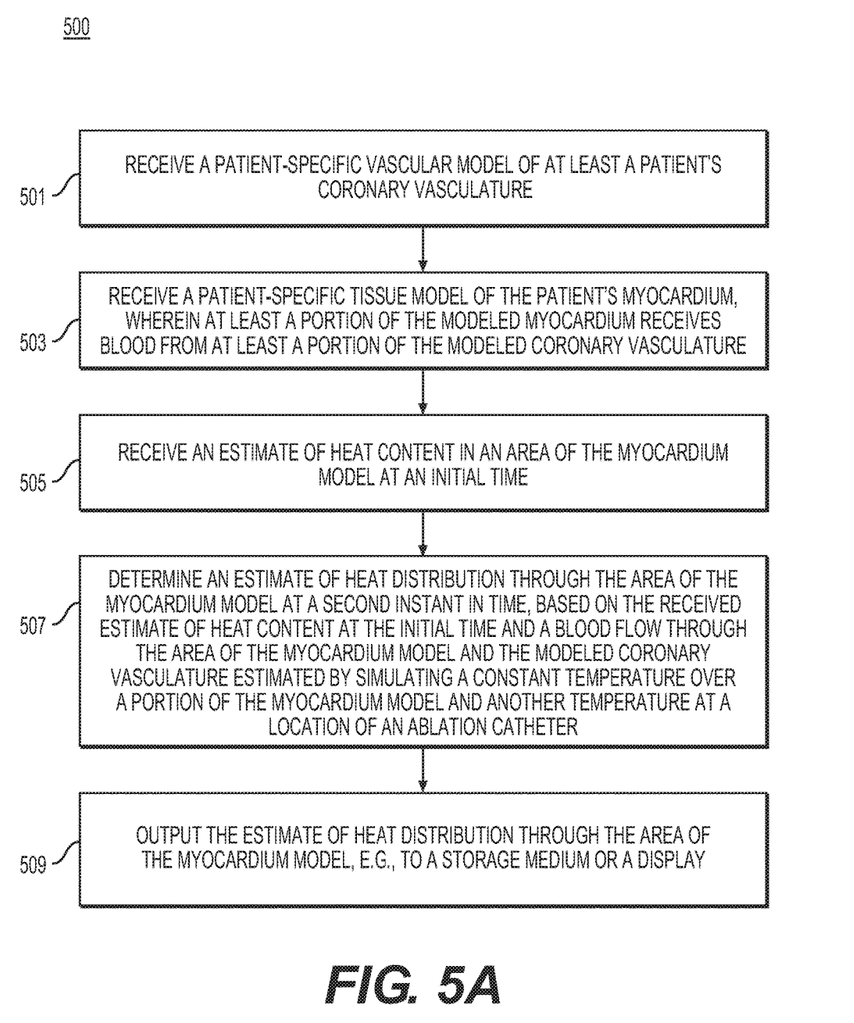
FIG. 5A is a flow diagram of an exemplary method of analyzing heat transfer in a patient's myocardium as a result of ablation, according to an exemplary embodiment of the present disclosure.
Figure 5B:
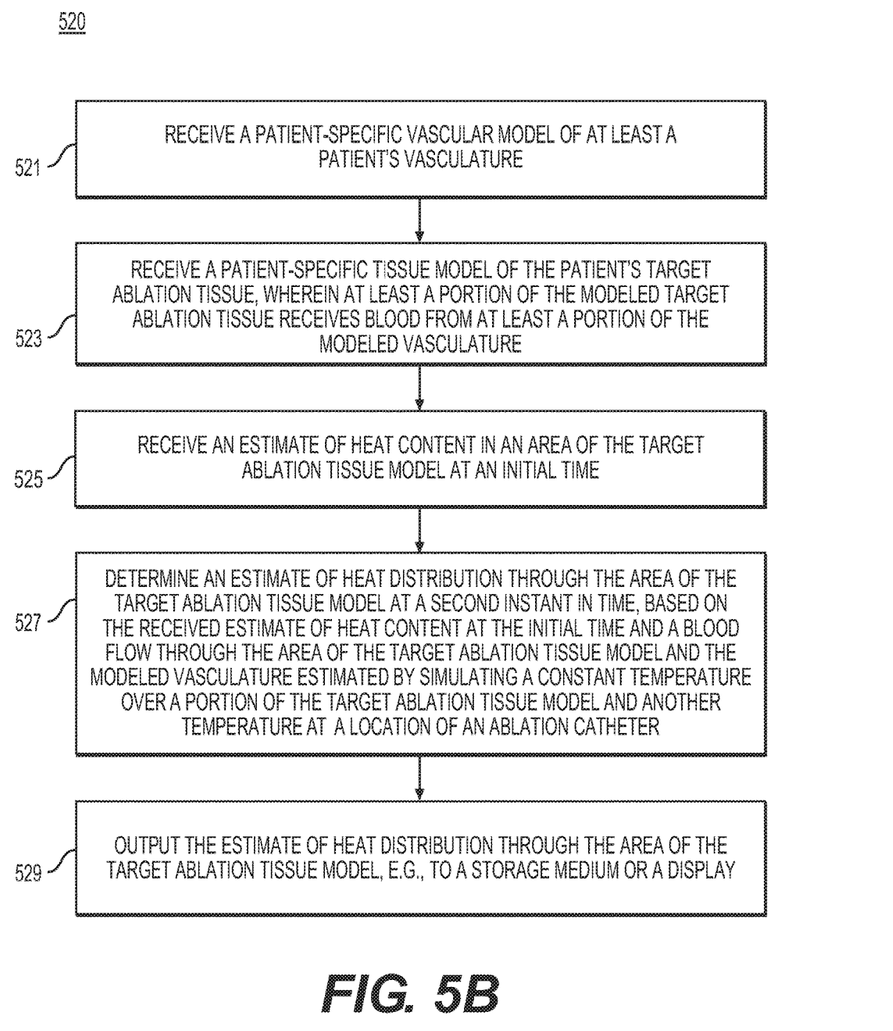
FIG. 5B is a flow diagram of an exemplary method of analyzing heat transfer in a patient's tissue as a result of ablation, according to an exemplary embodiment of the present disclosure.
Figure 6:
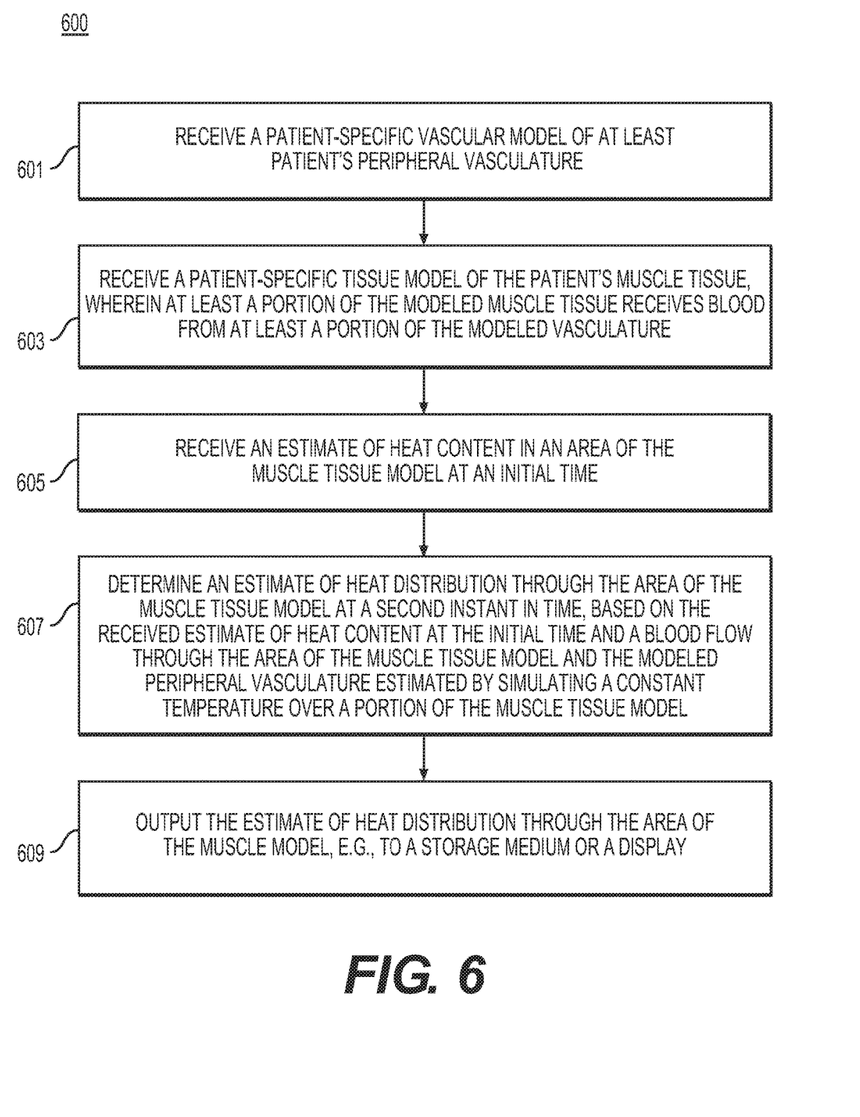
FIG. 6 is a flow diagram of an exemplary method of analyzing heat transfer in musculoskeletal tissue, according to an exemplary embodiment of the present disclosure.

FIG. 2 depicts a general embodiment of a method for estimating a heat distribution in a target tissue. FIG. 3 and FIG. 4 depict exemplary methods for evaluating heat transfer throughout a patient's entire body or portions thereof. For example, FIG. 3 shows an exemplary method for analyzing thermoregulation of a patient's body. FIG. 4 shows an exemplary method of analyzing a body's thermoregulation in association with a therapy that may include rapid cooling or heating in a portion of a patient's body. FIGS. 5A, 5B, and 6 depict exemplary methods for evaluating heat transfer in particular portions of a patient's body. For example, FIGS. 5A and 5B show exemplary methods for analyzing heat transfer from ablation in a patient's myocardium and/or in a patient's tissue, respectively. FIG. 6 depicts an exemplary method for heat transfer in musculoskeletal tissue, e.g., from a heating or cooling apparatus externally applied to a patient's skin. Heating or cooling apparatuses may include heating packs/pads or cooling packs, or electrical or other medical devices.

Any of the embodiments depicted in FIGS. 2-6 may be modified, for example, to include variations or changes of circulation, blood flow temperature, and/or patient anatomy. Changes in circulation may reflect scenarios where a physician may temporarily increase or decrease circulation locally (e.g., via a tourniquet, balloon catheter, hyperbaric chamber, etc.) in order to better control heat transfer in a patient and/or increase the safety of a procedure. In such an embodiment, any of the above methods may be modified to account for this increased or decreased circulation, e.g., by adjusting the blood flow simulation boundary conditions to reflect the modified circulation. Modified circulation may further include temporary stops to blood flow. For example, some surgery may involve halting blood flow for a period of time, e.g., inducing deep systemic hypothermia for cerebral/cardiac protection during the surgery. The disclosed systems and methods may be modified to model and assess any range of changes to circulation.

Another modification may include a modeling a bolus of heat/cold injected into the bloodstream, e.g., to change the local environment. This type of change may allow safer/more effective application or introduction of heat/cold to a patient's body. Such an embodiment may be computed, e.g., by introducing a differential heat/cold in the blood over a period of time when solving the advection-diffusion equation.

Furthermore, any of the exemplary methods depicted in FIGS. 2-6 may be used in conjunction with a modified patient model, including but not limited to a patient model modified to reflect revascularization or target tissue change in the patient's anatomy and/or a change in the parameters of the advection-diffusion equation.

FIG. 2 is a flow diagram of an exemplary method 200 of providing personalized estimates of bioheat transfer through a patient's body or a portion of a patient's body, according to an exemplary embodiment. The method of FIG. 2 may be performed by server systems 106, based on information, images, and data received from physicians 102 and/or third party providers 104 over electronic network 101.

In one embodiment, step 201 may include receiving an estimate of blood flow demand in at least a portion of a patient's body. For example, step 201 may include receiving a patient-specific vascular model in an electronic storage medium (e.g., hard drive, network drive, cloud drive, mobile phone, tablet, etc.) of the server systems 106. Specifically, receiving the patient-specific vascular model may include either generating the patient-specific vascular model at the server system 106, or receiving one over electronic network (e.g., electronic network 101). The vasculature may be obtained, for example, via imaging, including computed tomography (CT) or magnetic resonance (MR) imaging. The patient-specific vascular model may include an estimate of blood flow demand in one or more portions of the vascular model.

In one embodiment, step 203 may include receiving a patient-specific tissue model of at least the tissue in which heat transfer may be estimated. In one embodiment, the patient-specific tissue model may be received in an electronic storage medium. The tissue model and/or the tissue in which heat transfer may be estimated, may be referred to as, "target tissue."

In one embodiment, step 205 may include receiving an estimate of heat content, e.g., temperature, of one or more areas of the target tissue and/or surrounding environment (e.g., anatomical environment or patient environment). In one embodiment, a patient environment may include the surrounding environment may include an environment surrounding a target tissue, e.g., an environment around a patient's heart or brain that may influence temperature(s) within the patient's heart or brain). In one embodiment, the estimate of heat content may include a temperature of one or more areas of the target tissue and/or surrounding environment at one instant in time. For example, the instant in time may serve as an initial time (e.g., $T_0$). The temperature estimate of step 205 may include an initial temperature of the surrounding anatomical environment, e.g., as given by a (systemic) core heat. Such core heat may be derived from body temperature, activity level, etc.

In one embodiment, step 207 may include determining an estimate of the heat distribution of the target tissue and/or blood at a second instant in time based on the vascular model, target tissue model, and/or initial estimate of heat content. Step 207 may be performed using a processor (e.g., laptop, desktop, cloud computing architecture, graphics processing unit (GPU), digital signal processor (DSP), mobile phone, tablet, etc.).

In one embodiment, step 209 may include outputting the estimate of the heat distribution (e.g., of step 207) to an electronic storage medium and/or a user display (e.g., monitor, mobile phone, tablet). The user display may include rendering estimated heat distribution of the patient-specific vascular model and/or rendering estimated heat distribution of the target tissue (e.g., the tissue model). Step 209 may further include features comprising one or more of: simulations of heat distribution through the tissue model (e.g., color-coded temperature maps), interactive options or prompts to adjust circulation, temperature, or model geometry at any location in rendered vascular and/or tissue models, menu selections associated with various treatments to apply for modeling (including temperature-based and non-temperature-based treatments), options or suggestions to adjust time frames for heat distribution (e.g., recommendations of time intervals or times at which to perform follow-up assessments of bioheat changes), comparisons of various modeled bioheat scenarios (for a single patient and comparisons between patients), etc. Displays for comparisons may include overlays and/or side-by-side panels displaying various portions of the patient-specific vascular and/or tissue model.

FIGS. 3 and 4 depict analyses of heat transfer in a patient's body. In other words, the methods shown in FIGS. 3 and 4 may be relevant for studying thermoregulation. Thermoregulation is a metabolic function that may be challenged by conditions including hypothermia, hyperthermia, heat stroke, and/or heat exhaustion. An analysis of heat transfer in the patient's entire body may help evaluate the effectiveness of therapy to address one of these conditions or to develop new therapeutic methods for addressing these conditions. FIG. 3 shows an exemplary method of such an analysis of heat transfer. FIG. 4 shows an exemplary method of such an analysis of heat transfer in a patient's entire body, where the analysis may involve treating one or more of the metabolic conditions by, at least, employing a therapy that may apply rapid cooling and/or heating to a portion of the patient's body.

FIG. 3 is a flow diagram of an exemplary method 300 of analyzing heat transfer in a patient's body, according to an exemplary embodiment. The method of FIG. 3 may be performed by server systems 106, based on information, images, and data received from physicians 102 and/or third party providers 104 over electronic network 101.

In one embodiment, step 301 may include receiving a patient-specific vascular model of the patient's whole-body vasculature in an electronic storage medium (e.g., hard drive, network drive, cloud drive, mobile phone, tablet, etc.). This model may include large vessels (e.g., obtained via imaging, including CT and/or MR) and/or microvasculature perfusing the tissue. The microvasculature may be measured or simulated (e.g., generated via a constrained constructive optimization). The vascular model may include arteries, veins, or some combination of arteries and veins.

In one embodiment, step 303 may include receiving a patient-specific model of the patient's tissue, including organs and muscles (e.g., the target tissue) in an electronic storage medium. This model may be extracted from a medical imaging scan (e.g., via CT or MR imaging).

In one embodiment, step 305 may include receiving an estimate of heat content in one or more areas of the target tissue at one instant in time. In one embodiment, the target tissue may be estimated or modeled as homogeneous at a reduced (hypothermia) temperature and/or a raised (hyperthermia) temperature. Deep organs known to source heat during thermoregulation (e.g., liver, brain, and/or heart) may be initialized with a temperature closer to the patient's homeostatic temperature (e.g., 37° Celsius).

In one embodiment, step 307 may include determining an estimate of the heat distribution of the target tissue at a second instant in time based on the cardiovascular model, target tissue model, and/or initial estimate of heat content. In one embodiment, step 307 may include using a processor (e.g., laptop, desktop, cloud computing architecture, GPU, DSP, mobile phone, tablet, etc.) to determine the estimate of the heat distribution in the target tissue at the second instant in time.

For example, step 307 may include estimating the heat distribution by determining the blood flow in the vascular model (e.g., from step 301). Estimating blood flow may include an analysis involving 3D computational fluid dynamics, a reduced order model, and/or estimation from a database (e.g., using machine learning). Estimating blood flow may also include determining blood flow demand. For instance, step 307 may include performing a patient-specific estimate of blood flow in the patient's vasculature based on an estimate of blood flow demand (e.g., from the target tissue mass or total vascular volume). Blood flow demand may include volumetric flow rate, blood flow velocity, or velocity field (e.g., in a cross-section of a segment of a vessel or a portion of the target tissue). Blood flow demand may include the amount of blood flow sufficient for an organ to meet metabolic needs, e.g. the amount of blood flow provided by the myocardium to meet oxygen requirements during physical activity. Blood flow demand may be represented as a flow rate per unit of tissue or organ, and blood flow demand may be met by the flow rate through the vasculature supplying that tissue or organ. In other words, one embodiment of step 307 may include estimating blood flow demand of a tissue mass or vascular volume, determining blood flow to the tissue mass or through the vascular volume (given the blood flow demand of the respective tissue or vasculature), and estimating heat distribution through the tissue or vasculature from the determined blood flow.

One embodiment of determining heat distribution using blood flow may include arteriolar vasodilation and/or vasoconstriction modeling to reflect patient blood flow under various patient physiological states or external conditions. For example, the arteriolar vasodilation and/or vasoconstriction modeling may include modeling an increase of the skin perfusion in hyperthermic conditions or modeling a decrease skin perfusion in hypothermic conditions. The modeling of arteriolar vasodilation and/or vasoconstriction may be performed by reducing or increasing the resistance in a boundary condition model at one or more outlets of the supplying arterial system or, alternatively or in addition, by changing the caliber of an explicit microcirculation network model within the tissue itself, based on the temperature in the tissue or organ.

Heat distribution may be determined from blood flow by way of advection-diffusion equations. For example, step 307 may include determining patient-specific heat transfer by solving an advection-diffusion equation for the temperature in which an estimated blood flow velocity field (e.g., from an estimated blood flow and/or blood flow demand) may be assumed to provide advection of heat in the target tissue.

In some embodiments, patient heat transfer properties (e.g. conductivity) may be assigned from data acquired from imaging sources or literature. Another option may include assuming uniform material properties in the target tissue. Boundary conditions for modeling patient-specific heat transfer may be applied at the skin boundaries (e.g., using Dirichlet boundary conditions for the room temperature and modeling a loss at the skin boundary due to sweat evaporation during hyperthermic conditions). In some cases, the heat transfer equation (advection-diffusion equation) may be solved for a fixed time (e.g., several seconds) or for a steady-state solution to produce an estimated heat distribution at one or more additional time instants.

In one embodiment, step 309 may include outputting the one or more estimated heat distributions in the target tissue, e.g., to an electronic storage medium or a user display (e.g., monitor, mobile phone, tablet, etc.).

FIG. 4 is a flow diagram of an exemplary method 400 of analyzing heat transfer in a patient's body where body temperature may rapidly change, according to an exemplary embodiment. The method of FIG. 4 may be performed by server systems 106, based on information, images, and data received from physicians 102 and/or third party providers 104 over electronic network 101.

In one embodiment, step 401 may include receiving a patient-specific vascular model of the whole-body vasculature in an electronic storage medium (e.g., hard drive, network drive, cloud drive, mobile phone, tablet, etc.). This model may include large vessels (e.g., obtained via imaging such as CT or MR) and/or microvasculature perfusing the tissue. The microvasculature may be measured and/or simulated (e.g., via a constrained constructive optimization). The vascular model may include arteries, veins, or some combination of arteries and veins.

In one embodiment, step 403 may include receiving a patient-specific model of the patient tissue, including organs and muscles (the target tissue) in an electronic storage medium. This model may be extracted from a medical imaging scan (e.g., CT or MR).

In one embodiment, step 405 may include receiving an estimate of heat content in one or more areas of the target tissue at one instant in time. In one embodiment, the target tissue may be estimated or modeled as homogeneous at a reduced (hypothermia) temperature and/or at a raised (hyperthermia) temperature. Deep organs known to source heat during thermoregulation (e.g., liver, brain and heart) may be initialized with a temperature closer to the homeostatic temperature (e.g., 37° Celsius).

In one embodiment, step 407 may include determining an estimate of the heat distribution in the target tissue at a second instant in time based on the cardiovascular model, target tissue model, and/or initial estimate of heat content. In one embodiment, step 407 may include using a processor (e.g., laptop, desktop, cloud computing architecture, GPU, DSP, mobile phone, tablet, etc.) to determine the estimate of the heat distribution in the target tissue at the second instant in time.

The estimate of blood flow may be determined by first determining the blood flow in the cardiovascular model in a simulated physiological state. For instance, step 407 may include performing a patient-specific estimate of blood flow in the patient's vasculature using an estimate of the patient's blood flow demand (e.g., from the target tissue mass or total vascular volume). Estimating blood flow may include analyzing 3D computational fluid dynamics, a reduced order model, or blood flow estimates from a database (e.g., using machine learning). One embodiment of determining heat distribution using blood flow may include arteriolar vasodilation and/or vasoconstriction modeling to reflect patient blood flow under various patient physiological states or external conditions. For example, the arteriolar vasodilation and/or vasoconstriction modeling may include modeling an increase of the skin perfusion in hyperthermic conditions or modeling a decrease skin perfusion in hypothermic conditions.

In one embodiment, a patient-specific heat transfer may be determined by solving an advection-diffusion equation. For example, step 407 may include solving an advection-diffusion equation for the concentration of heat in which the estimated blood flow velocity field (e.g., from an estimated blood flow and/or blood flow demand) may be assumed to provide advection in the target tissue.

Step 407 of estimating the heat distribution may include setting one or more conditions for determining the estimate. For example, patient heat transfer properties (e.g., diffusivity) may be assigned from data acquired from imaging sources or literature. Another option for setting conditions to estimate heat distribution may include assuming uniform material properties in the target tissue. Boundary conditions may be applied at the skin boundaries (e.g., using Dirichlet boundary conditions for the room temperature and modeling a loss at the skin boundary due to sweat evaporation during hyperthermic conditions). In particular, the applied heat/cooling source may be virtually applied as a Dirichlet boundary condition fixing a constant temperature (e.g., hot or cold, depending on the device) over the portion of skin affected by the source. The heat transfer equation may be solved for a fixed time (e.g., several seconds) or for a steady-state solution to produce an estimated heat distribution at one or more additional time instants.

In one embodiment, step 409 may include outputting the one or more estimated heat distributions in the target tissue, e.g., to an electronic storage medium or a user display (e.g., monitor, mobile phone, tablet, etc.).

FIGS. 5A, 5B, and 6 include exemplary analyses of local heat transfer in, at least, portions of a patient's body. For example, exemplary methods of FIGS. 5A and 5B include analyses of heat transfer in connection with ablation in various parts of a patient's body. FIG. 5A includes an exemplary method for analyzing heat transfer in the myocardium associated with ablation. An analysis of heat transfer in the myocardium may assess the effectiveness of an RF ablation or cryoablation procedure (e.g., for treating left ventricular tachycardia, supraventricular tachycardia, Wolff-Parkinson-White syndrome, atrial tachycardia, multifocal atrial tachycardia or atrial fibrillation) and/or to determine preferable or optimal settings for the ablation. FIG. 5B includes an exemplary method for analyzing heat transfer in tissue (e.g., organ tissue) associated with ablation. An analysis of heat transfer in organ tissue may help assess the effectiveness of an RF ablation, cryoablation, ablation performed using external beam radiation or high frequency ultrasound (HIFU), cryogenic, and/or cryotherapy treatment procedure (e.g., for treating cancer of the liver, bone, lung, spleen, skin, prostate or kidney by destroying tumors or lesions). The exemplary method described in FIG. 6 includes analyses of heat transfer in musculoskeletal tissue. An analysis of heat transfer in the musculoskeletal tissue may be useful, e.g., in sports medicine to assess the effectiveness of heat transfer from a heating or cooling apparatus applied to the exterior of the skin to a patient's muscles. Such an analysis may help determine settings for heating/cooling apparatus size, temperature, and/or location as well as assist in the design of more effective heating/cooling apparatuses.

FIG. 5A is a flow diagram of an exemplary method 500 of analyzing heat transfer in a patient's myocardium associated with ablation, according to an exemplary embodiment. The method of FIG. 5A may be performed by server systems 106, based on information, images, and data received from physicians 102 and/or third party providers 104 over electronic network 101.

In one embodiment, step 501 may include receiving a patient-specific coronary vascular model in an electronic storage medium (e.g., hard drive, network drive, cloud drive, mobile phone, tablet, etc.). This model may include large coronary vessels (e.g., obtained via imaging, including CT and/or MR) and/or include microvasculature perfusing the tissue. The microvasculature may be measured or simulated (e.g., via a constrained constructive optimization). The vascular model may include arteries, veins, or some combination of arteries and veins.

In one embodiment, step 503 may include receiving a patient-specific model of the patient tissue, including the myocardium (or epicardium, atrial wall, etc.) as the target tissue in an electronic storage medium. This model may be extracted from a medical imaging scan (e.g., CT and/or MR).

In one embodiment, step 505 may include receiving an estimate of heat content in one or more areas of the target tissue at one instant in time. In one embodiment, the target tissue may be estimated or modeled as homogeneous at body temperature, except for the location of an ablation catheter which may be set to a prespecified temperature in a localized area (e.g., at a temperature of 50° Celsius in an area of 4 mm for RF ablation or a temperature of −10° to −70° Celsius for cryoablation). The ablation catheter location in the target tissue may be represented virtually (e.g., for pre-procedure simulation and planning) or may be represented in its actual location during a procedure (e.g., using positioning on the catheter tip).

In one embodiment, step 507 may include determining an estimate of the heat distribution in the target tissue and/or blood at a second instant in time based on the cardiovascular model, target tissue model, and/or initial estimate of heat content. In one embodiment, step 507 may include using a processor (e.g., laptop, desktop, cloud computing architecture, GPU, DSP, mobile phone, tablet, etc.) to determine the estimate of the heat distribution in the target tissue at the second instant in time.

The estimate may be determined by first determining the blood flow in the cardiovascular model in a simulated physiological state. For instance, step 507 may include performing a patient-specific estimate of blood flow in the patient's coronaries using an estimate of the patient's blood flow demand. The blood flow demand may include the blood flow demand from the total vascular volume or the myocardial mass (e.g., the mass of the target tissue). Estimating blood flow may include analyzing 3D computational fluid dynamics, a reduced order model, or blood flow estimates from a database (e.g., using machine learning).

In one embodiment, a patient-specific heat transfer may be determined by solving an advection-diffusion equation. For example, step 507 may include solving an advection-diffusion equation for the concentration of heat in which the estimated blood flow velocity field (e.g., from an estimated blood flow and/or blood flow demand) may be assumed to provide advection in the target tissue.

Step 507 of estimating the heat distribution may include setting one or more conditions for determining the estimate. For example, patient heat transfer properties (e.g., diffusivity) may be assigned from data acquired from imaging sources or literature. Another option may including assuming uniform material properties in the target tissue. Boundary conditions may be applied at the endocardial and epicardial surfaces using empirically-derived values (e.g., using Dirichlet boundary conditions with a homeostatic temperature for the endocardium and epicardium) and/or by coupling to another computational model (e.g., a heat-transfer model in the whole body or a pulsatile blood flow model in a dynamic heart). The heat transfer equation may be solved for a fixed time (e.g., several seconds) or for a steady-state solution to produce an estimated heat distribution, e.g., at one or more additional time instants.

In one embodiment, step 509 may include outputting the one or more estimated heat distributions in the target tissue, e.g., to an electronic storage medium or a user display (e.g., monitor, mobile phone, tablet, etc.).

FIG. 5B is a flow diagram of an exemplary method 520 of analyzing heat transfer in tissue associated with ablation, according to an exemplary embodiment. The method of FIG. 5B may be performed by server systems 106, based on information, images, and data received from physicians 102 and/or third party providers 104 over electronic network 101.

In one embodiment, step 521 may include receiving a patient-specific vascular model of the vasculature in the target tissue and/or surrounding tissue in an electronic storage medium (e.g., hard drive, network drive, cloud drive, mobile phone, tablet, etc.). This model may include large vessels (e.g., obtained via imaging such as CT or MR) and/or include microvasculature perfusing the tissue. The microvasculature may be measured or simulated (e.g., via a constrained constructive optimization). The vascular model may include arteries, veins, or some combination of arteries and veins.

In one embodiment, step 523 may include receiving a patient-specific model of target ablation tissue (e.g., the tissue containing a tumor or lesion) as the target tissue in an electronic storage medium. In some embodiments, the tissue may include organ tissue, e.g., liver tissue, lung tissue, and/or kidney tissue. This model may be extracted from a medical imaging scan (e.g., CT or MR).

In one embodiment, step 525 may include receiving an estimate of heat content in one or more areas of the target tissue at one instant in time. In one embodiment, the target tissue may be estimated or modeled as homogeneous at body temperature, except for the location of an ablation catheter which is set to a prespecified temperature in a localized area (e.g., at a temperature of 50° Celsius in an area of 4 mm for RF ablation or a temperature of −10° to −70° Celsius for cryoablation). The temperature at which the body may be modeled, may be derived from the ambient temperature and/or via a systemic temperature controlled to make the localized heating/cooling safer for the patient. The ablation catheter location in the target tissue may be represented virtually (e.g., for pre-procedure simulation and planning) or may be represented in its actual location during a procedure (e.g., using positioning on the catheter tip).

In one embodiment, step 527 may include determining an estimate of the heat distribution in the target tissue and/or blood at a second instant in time based on the vascular model, target tissue model, and/or initial estimate of heat content. In one embodiment, step 527 may include using a processor (e.g., laptop, desktop, cloud computing architecture, GPU, DSP, mobile phone, tablet, etc.) to determine the estimate of the heat distribution in the target tissue at the second instant in time.

The estimate of the heat distribution may be determined by determining the blood flow in the vascular model in a simulated physiological state. For instance, step 527 may include performing a patient-specific estimate of blood flow in the patient's vasculature using an estimate of the patient's blood flow demand (e.g., from the target tissue mass or total vascular volume). Estimating blood flow may include analyzing 3D computational fluid dynamics, a reduced order model, or blood flow estimates from a database (e.g., using machine learning).

In one embodiment, a patient-specific heat transfer may be determined by solving an advection-diffusion equation. For example, step 527 may include solving an advection-diffusion equation for the concentration of heat in which the estimated blood flow velocity field (e.g., from an estimated blood flow and/or blood flow demand) may be assumed to provide advection in the target tissue.

Step 527 of estimating the heat distribution may include setting one or more conditions for determining the estimate. For example, patient heat transfer properties (e.g. diffusivity) may be assigned from data acquired from imaging sources or literature. Another option may include assuming uniform material properties in the target tissue. Boundary conditions may be applied at the endocardial and epicardial surfaces using empirically-derived values (e.g., using Dirichlet boundary conditions with a homeostatic temperature for the target tissue surface) and/or by coupling to another computational model (e.g., a heat-transfer model in the whole body including multiple organs, fat, fluid, bone, etc.). The heat transfer equation may be solved for a fixed time (e.g., several seconds) or for a steady-state solution to produce an estimated heat distribution, e.g., at one or more additional time instants.

In one embodiment, step 529 may include outputting the one or more estimated heat distributions in the target tissue, e.g., to an electronic storage medium or a user display (e.g., monitor, mobile phone, tablet, etc.).

FIG. 6 is a flow diagram of an exemplary method 600 of analyzing heat transfer in musculoskeletal tissue, according to an exemplary embodiment. The method of FIG. 6 may be performed by server systems 106, based on information, images, and data received from physicians 102 and/or third party providers 104 over electronic network 101.

In one embodiment, step 601 may include receiving a patient-specific peripheral vascular model in an electronic storage medium (e.g., hard drive, network drive, cloud drive, mobile phone, tablet, etc.). This model may include one or more of the large peripheral vessels (e.g., obtained via imaging such as CT or MR) and/or including microvasculature perfusing the target muscle tissue and/or microvasculature perfusing the body exterior (e.g., skin). The microvasculature may be measured or simulated (e.g., via a constrained constructive optimization). The vascular model may include arteries, veins, or some combination of arteries and veins.

In one embodiment, step 603 may include receiving a patient-specific model of target muscle tissue (e.g., the quadriceps femoris or any other arm, leg, hip, hand or foot muscle) as the target tissue in an electronic storage medium. This model may be extracted from a medical imaging scan (e.g., CT or MR). For a more comprehensive model, the target tissue may be taken as a particular muscle and the surrounding muscle, bone, fat, and fluid. The initial temperature of the surrounding muscle, bone, fat, and fluid may be given by a (systemic) core heat derived from body temperature, activity level, etc.

In one embodiment, step 605 may include receiving an estimate of heat content in one or more areas of the target tissue at one instant in time. In one embodiment, the target tissue may be estimated or modeled as homogeneous at body temperature, except for the location of the heating/cooling apparatus in a localized area of the body exterior. The heating/cooling apparatus location in the target tissue may be represented virtually (e.g., for pre-application simulation and planning) or may be represented in its actual location during an application (e.g., using positioning on the catheter tip). In one embodiment, the temperature at which the body may be modeled may be derived from the ambient temperature.

In one embodiment, step 607 may include determining an estimate of the heat distribution in the target tissue at a second instant in time based on the vascular model, target tissue model, and/or initial estimate of heat content. In one embodiment, step 607 may include using a processor (e.g., laptop, desktop, cloud computing architecture, GPU, DSP, mobile phone, tablet, etc.) to determine the estimate of the heat distribution in the target tissue at the second instant in time.

The estimate may be determined by determining the blood flow in the cardiovascular model in a simulated physiological state. For instance, step 607 may include performing a patient-specific estimate of blood flow in the patient's coronaries using an estimate of the patient's blood flow demand (e.g., from the target muscle mass or total vascular volume). Estimating blood flow may include analyzing 3D computational fluid dynamics, a reduced order model, and/or blood flow estimates from a database (e.g., using machine learning).

In one embodiment, a patient-specific heat transfer may be determined by solving an advection-diffusion equation. For example, step 607 may include solving an advection-diffusion equation for the concentration of heat in which the estimated blood flow velocity field (e.g., from an estimated blood flow and/or blood flow demand) may be assumed to provide advection in the target tissue.

Step 607 of estimating the heat distribution may include setting one or more conditions for determining the estimate. For example, patient heat transfer properties (e.g., diffusivity) may be assigned from data acquired from imaging sources or literature. Another option may including assuming uniform material properties in the target tissue. Boundary conditions may be applied at the target tissue surface using empirically-derived values and/or estimated values, e.g., based on core temperature, activity levels, and/or coupling to another computational model (e.g., a heat-transfer model in the whole body or a pulsatile blood flow model in a dynamic heart). Alternatively or in addition, boundary conditions may be applied in a wider field of view (e.g., applied a homeostatic body temperature boundary condition at the borders of a larger anatomical model encompassed, for example, by the entire field of view of a medical image). The heat transfer equation may be solved for a fixed time (e.g., several seconds) and/or for a steady-state solution. One or more solutions from the heat transfer equation may be used to produce an estimated heat distribution at one or more additional time instants.

In one embodiment, step 609 may include outputting the one or more estimated heat distributions in the target tissue, e.g., to an electronic storage medium or a user display (e.g., monitor, mobile phone, tablet, etc.).

The ability of bodies to regulate temperature or respond to temperature changes may vary between individuals. Temperature-related conditions may negatively impact a patient (e.g., causing hypothermia or hyperthermia), or temperature may be used to treat a patient (e.g., in treating hypothermia/hyperthermia or in ablation). Different patients may respond to temperature and treatment differently, depending on the unique ways that each patient's body may conduct bioheat transfer. The present disclosure includes systems and methods for determining bioheat transfer specific to an individual. For example, the disclosure includes systems and methods for modeling bioheat transfer specifically for the individual's anatomy, as extracted from patient-specific imaging. For instance, the present disclosure includes an exemplary embodiment of modeling patient-specific bioheat transfer by estimating heat diffusion from blood flow through the patient's anatomy. An understanding of patient-specific bioheat transfer may improve treatment efficacy for temperature-related ailments and treatments.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of providing personalized estimates of bioheat transfer through a patient's body or a portion of a patient's body, the method comprising:
   receiving a patient-specific vascular model of a patient's anatomy, including at least one vessel outlet of the patient;
   receiving a patient-specific tissue model of at least a portion of tissue of the patient's anatomy;
   receiving an estimate of heat content of the portion of tissue of the patient-specific tissue model or tissue surrounding the portion of tissue;
   receiving a physiological state of interest at which to simulate blood flow through the patient-specific vascular model and/or patient-specific tissue model of the patient;
   simulating the received physiological state of interest for the patient by generating, for the received physiological state of interest, a patient-specific boundary condition model of the at least one vessel outlet of the patient-specific vascular model;
   computing a value of blood flow through the patient-specific vascular model or to the patient-specific tissue model at the simulated physiological state of interest using the generated patient-specific boundary condition model corresponding to the received physiological state of interest;
   estimating a value of heat distribution of the portion of tissue of the patient-specific tissue model or tissue surrounding the portion of tissue using the received estimate of heat content and the value of blood flow corresponding to the simulated physiological state of interest; and
   outputting the determined estimate of heat distribution to a storage medium or user display.

2. The computer-implemented method of claim 1, wherein the estimate of heat content of the portion of tissue comprises the heat content of the portion of tissue or the surrounding tissue at a first point of time; and
   wherein the estimate of heat distribution comprises heat distribution at a second point of time different from the first point of time.

3. The computer-implemented method of claim 1, wherein the estimate of heat content is estimated as a homogenous value.

4. The computer-implemented method of claim 3, further comprising:
   determining an introduction of a temperature source in a location of the tissue model or vascular model, wherein the estimate of heat content is homogenous except for the location of the temperature source.

5. The computer-implemented method of claim 4, wherein the temperature source is associated with ablation, a heating apparatus, or a cooling apparatus.

6. The computer-implemented method of claim 1, wherein the value of blood flow comprises a value characterizing a blood flow demand for an organ or a volume of tissue to meet its metabolic needs, a volumetric flow rate, a blood flow velocity, or a blood flow velocity field.

7. The computer-implemented method of claim 1, further comprising:
   determining the estimate of heat distribution using a heat transfer equation.

8. The computer-implemented method of claim 1, wherein the vascular model includes large vessels and microvasculature of the patient's anatomy.

9. A system for providing personalized estimates of bioheat transfer through a patient's body or a portion of a patient's body, the system comprising:
   a data storage device storing instructions of providing personalized estimates of bioheat transfer through a patient's body or a portion of a patient's body; and
   a processor configured to execute the instructions to perform a method including:
      receiving a patient-specific vascular model of a patient's anatomy, including at least one vessel outlet of the patient;
      receiving a patient-specific tissue model of at least a portion of tissue of the patient's anatomy;
      receiving an estimate of heat content of the portion of tissue of the patient-specific tissue model or tissue surrounding the portion of tissue;
      receiving a physiological state of interest at which to simulate blood flow through the patient-specific vascular model and/or patient-specific tissue model of the patient;
      simulating the received physiological state of interest for the patient by generating, for the received physiological state of interest, a patient-specific boundary condition model of the at least one vessel outlet of the patient-specific vascular model;
      computing a value of blood flow through the patient-specific vascular model or to the patient-specific tissue model at the simulated physiological state of interest using the generated patient-specific boundary condition model corresponding to the received physiological state of interest;
      estimating a value of heat distribution of the portion of tissue of the patient-specific tissue model or tissue surrounding the portion of tissue using the received estimate of heat content and the value of blood flow corresponding to the simulated physiological state of interest; and
      outputting the determined estimate of heat distribution to a storage medium or user display.

10. The system of claim 9, wherein the estimate of heat content of the portion of tissue comprises the heat content of the portion of tissue or the surrounding tissue at a first point of time; and
   wherein the estimate of heat distribution comprises heat distribution at a second point of time different from the first point of time.

11. The system of claim 9, wherein the estimate of heat content is estimated as a homogenous value.

12. The system of claim 11, wherein the system is further configured for:
   determining an introduction of a temperature source in a location of the tissue model or vascular model, wherein the estimate of heat content is homogenous except for the location of the temperature source.

13. The system of claim 12, wherein the temperature source is associated with ablation, a heating apparatus, or a cooling apparatus.

14. The system of claim 9, wherein the value of blood flow comprises a value characterizing a blood flow demand for an organ or a volume of tissue to meet its metabolic needs, a volumetric flow rate, a blood flow velocity, or a blood flow velocity field.

15. The system of claim 9, wherein the system is further configured for:
   determining the estimate of heat distribution using a heat transfer equation.

16. The system of claim 9, wherein the vascular model includes large vessels and microvasculature of the patient's anatomy.

17. A non-transitory computer readable medium for use on a computer system containing computer-executable programming instructions for performing a method of providing personalized estimates of bioheat transfer through a patient's body or a portion of a patient's body, the method comprising:
   receiving a patient-specific vascular model of a patient's anatomy, including at least one vessel outlet of the patient;
   receiving a patient-specific tissue model of at least a portion of tissue of the patient's anatomy;
   receiving an estimate of heat content of the portion of tissue of the patient-specific tissue model or tissue surrounding the portion of tissue;
   receiving a physiological state of interest at which to simulate blood flow through the patient-specific vascular model and/or patient-specific tissue model of the patient;
   simulating the received physiological state of interest for the patient by generating, for the received physiological state of interest, a patient-specific boundary condition model of the at least one vessel outlet of the patient-specific vascular model;
   computing a value of blood flow through the patient-specific vascular model or to the patient-specific tissue model at the simulated physiological state of interest using the generated patient-specific boundary condition model corresponding to the received physiological state of interest;
   estimating a value of blood flow corresponding to the received physiological state of interest by computing the value of blood flow using the patient-specific boundary condition model;
   estimating a value of heat distribution of the portion of tissue of the patient-specific tissue model or tissue surrounding the portion of tissue using the received estimate of heat content and the value of blood flow corresponding to the simulated physiological state of interest; and
   outputting the determined estimate of heat distribution to a storage medium or user display.

18. The non-transitory computer readable medium of claim 17, wherein the estimate of heat content of the portion of tissue comprises the heat content of the portion of tissue or the surrounding tissue at a first point of time; and
   wherein the estimate of heat distribution comprises heat distribution at a second point of time different from the first point of time.

19. The non-transitory computer readable medium of claim 17, wherein the estimate of heat content is estimated as a homogenous value.

20. The non-transitory computer readable medium of claim 19, the method further comprising:
   determining an introduction of a temperature source in a location of the tissue model or vascular model, wherein the estimate of heat content is homogenous except for the location of the temperature source.

* * * * *